(12) United States Patent
Scalise et al.

(10) Patent No.: US 10,729,520 B2
(45) Date of Patent: Aug. 4, 2020

(54) METHOD AND DRILLS FOR TWO STAGE PROTOCOL FOR CREATING AN OSTEOTOMY FOR A DENTAL IMPLANT

(71) Applicant: Biomet 3i, LLC, Palm Beach Gardens, FL (US)

(72) Inventors: Michael D. Scalise, West Palm Beach, FL (US); Andre J Castillo, Jupiter, FL (US); Miguel G. Montero, Boynton Beach, FL (US); Dan P. Rogers, Palm Beach Gardens, FL (US); Ross W Towse, San Marcos, CA (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 9 days.

(21) Appl. No.: 13/760,644

(22) Filed: Feb. 6, 2013

(65) Prior Publication Data
US 2014/0220508 A1 Aug. 7, 2014

(51) Int. Cl.
| | |
|---|---|
| A61C 8/00 | (2006.01) |
| A61C 19/02 | (2006.01) |
| A61C 3/02 | (2006.01) |
| A61C 3/04 | (2006.01) |

(52) U.S. Cl.
CPC .............. *A61C 8/0089* (2013.01); *A61C 3/02* (2013.01); *A61C 3/04* (2013.01); *A61C 8/0087* (2013.01); *A61C 19/02* (2013.01)

(58) Field of Classification Search
CPC ....... A61C 8/0089; A61C 8/0087; A61C 3/02; A61C 3/04; A61C 19/02
USPC .......................................... 433/77, 165, 215
See application file for complete search history.

(56) References Cited

U.S. PATENT DOCUMENTS

| | | | | |
|---|---|---|---|---|
| 4,474,556 A | * | 10/1984 | Ellis et al. ..................... | 433/173 |
| 5,217,372 A | * | 6/1993 | Truocchio ..................... | 433/215 |
| 5,226,536 A | * | 7/1993 | Elliott ........................... | 206/369 |
| 5,261,818 A | * | 11/1993 | Shaw ................... | A61C 8/0089 |
| | | | | 433/165 |
| 5,320,529 A | * | 6/1994 | Pompa ........................... | 433/76 |

(Continued)

FOREIGN PATENT DOCUMENTS

WO WO-0185051 A2 11/2001

OTHER PUBLICATIONS

Nobel Biocare 2012 Product Catalog (http://files.nobelbiocare.com/FlipPdf/product_catalog_2012/files/74575_product-catalog%202012_gb.pdf), pp. 10-11, 18-19, 36-40, 70-71 and 112-113.
MIS Implants Technologies Ltd Combo package, Web page (http://www.mis-implants.com/Products/Implants/cl.aspx), accessed Sep. 11, 2013.

(Continued)

*Primary Examiner* — Cris L. Rodriguez
*Assistant Examiner* — Hao D Mai
(74) *Attorney, Agent, or Firm* — Schwegman Lundberg & Woessner, P.A.

(57) ABSTRACT

A dental protocol for creating an osteotomy for an implant is disclosed. A first drill is selected having a tip to create a pilot hole in the bone surface of a patient. The first drill includes a first boring section to create a bore hole for a second drill and a second boring section to create a coronal area on the hole near the bone surface. A first drill hole is created on the bone surface having a depth compatible with the length of the implant with the first drill and a coronal area. A second drill for creating a second hole having a width compatible with the body of the implant is selected. A second drill hole is created on the bone surface with the second drill.

26 Claims, 7 Drawing Sheets

(56) References Cited

U.S. PATENT DOCUMENTS

| | | | |
|---|---|---|---|
| 5,741,267 A * | 4/1998 | Jorneus et al. | 606/102 |
| 5,890,897 A * | 4/1999 | Kruger et al. | 433/75 |
| 6,237,451 B1 | 5/2001 | Wei | |
| 6,405,865 B1 | 6/2002 | Lin | |
| 6,514,258 B1 * | 2/2003 | Brown et al. | 606/80 |
| 6,783,004 B1 * | 8/2004 | Rinner | 206/368 |
| 6,863,529 B2 * | 3/2005 | Strong et al. | 433/165 |
| 8,038,440 B2 * | 10/2011 | Swaelens et al. | 433/76 |
| 8,342,841 B2 * | 1/2013 | Vogel et al. | 433/77 |
| 2002/0172923 A1 * | 11/2002 | Strong et al. | 433/165 |
| 2004/0063067 A1 * | 4/2004 | Takahashi | A61B 17/1673 433/165 |
| 2004/0200748 A1 * | 10/2004 | Klassen et al. | 206/368 |
| 2006/0111724 A1 * | 5/2006 | Yeung Wai Ping | A61B 17/1635 606/80 |
| 2006/0210949 A1 | 9/2006 | Stoop | |
| 2009/0200188 A1 * | 8/2009 | Kaczorowski et al. | 206/368 |
| 2009/0236249 A1 * | 9/2009 | Erskine-Smith | 206/368 |
| 2010/0009314 A1 * | 1/2010 | Tardieu et al. | 433/144 |
| 2010/0028828 A1 * | 2/2010 | Vogel et al. | 433/77 |

OTHER PUBLICATIONS

Glidewell's Tooth Replacement Systems webpage (https://www.inclusivedental.com/), accessed Sep. 11, 2013.

Biomet 3i Surgical Manual. Online. Aug. 2008 (URL:http://web.archive.org/web/20120321010632/http://biomet3i.com/Pdf/CATSM.pdf. Entire document.

Written Opinion of the International Searching Authority for related application PCT/US2014/014786, dated Apr. 7, 2014 (5 pp).

International Search Report for related application PCT/US2014/014786, dated Apr. 30, 2014 (4pp).

"European Application Serial No. 14749185.6, Response filed Oct. 26, 2017 to Extended European Search Report dated Jan. 30, 2017", 9 pgs.

"European Application Serial No. 14749185.6, Extended European Search Report dated Jan. 30, 2017", 9 pgs.

"European Application Serial No. 14749185.6, Communication Pursuant to Article 94(3) EPC dated Dec. 18, 2018", 4 pgs.

"European Application Serial No. 14749185.6, Response filed Apr. 25, 2019 to Communication Pursuant to Article 94(3) EPC dated Dec. 18, 2018", 16 pgs.

* cited by examiner

METHOD AND DRILLS FOR TWO STAGE PROTOCOL FOR CREATING AN OSTEOTOMY FOR A DENTAL IMPLANT

TECHNICAL FIELD

This disclosure relates to osteotomy drilling protocols and more specifically to a process and drills for a two stage osteotomy protocol.

BACKGROUND

A well-known procedure is the dental restoration of a partially or wholly edentulous patient with artificial dentition. Typically, a dental implant is seated into the bone of a patient's jaw. The dental implant includes a socket, e.g., a bore, which is accessible through the overlying or surrounding gum tissue for receiving and supporting one or more attachments or components which, in turn, are useful to fabricate and support prosthodontic restorations. The dental implant generally includes a threaded bore to receive a retaining screw for holding mating components therein. Dental implant procedures may use a variety of implanting modalities, for example, blade, threaded implant, or smooth push-in implant.

The process of seating the dental implant typically requires an incision being made through the gingiva to expose the underlying bone. The dental implant acts as an artificial tooth root when placed in the jawbone for integration. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

The process of preparing the first stage for the dental implant involves creating an osteotomy in the bone of the patient. Typically the osteotomy is created by using a series of drills in order to provide the proper shaped osteotomy to accommodate the dental implant. Implants have different width and length dimensions for different bone volumes and anatomical features. Implants also may have different body shapes to assist in fit with the bone. Each implant having selected dimensions requires distinct drills specific to the implant dimensions to create the appropriate osteotomy. In current drill protocols to create osteotomies for implants, multiple drills are necessary to create the desired osteotomy. For example, in the case of an existing protocol for a straight walled 4 mm width and 10 mm length implant, five separate drills are required. Once the site of the osteotomy has been determined, a first starter drill is used to locate the osteotomy and the site is marked by penetrating the bone surface with the starter drill to create a starting hole so the subsequent drills will not walk. The marked spot is used to locate a second twist drill which is used to create a hole to the depth of the implant. A third drill is used to widen the hole in medium or dense bone to create a coronal aspect to accept the body of the next drill. A fourth twist drill is used to shape the hole for the body of the implant. A final drill is used to widen the top of the osteotomy to accommodate a cover screw for the top of the implant.

The present protocols for creating osteotomies for a dental implant are cumbersome to implement as they require a clinician to perform multiple drilling steps. This is also time consuming and requires multiple drills which also results in patient discomfort. Further, the more drilling steps that are utilized increases risking contamination of the bone area. As there are different types of implants with different width and length dimensions for the variety of anatomical areas, the number of drills required for different patients increases.

It would be desirable to provide a drill protocol to create an osteotomy tailored to a specific implant. There is also a need for drills which can perform multiple functions previously requiring multiple drills in a protocol to create an osteotomy. It would also be desirable to provide packaging of drills that create an osteotomy matching the dimensions of a specific implant along with the implant to be used.

BRIEF SUMMARY

An example of the present disclosure is a method of creating an osteotomy on a bone surface for seating a dental implant having a body insertable in the osteotomy and a length. The method includes selecting a first drill having a tip to create a pilot hole, a first boring section to create a first bore hole for a second drill and a second boring section to create a coronal area on the hole near the bone surface. A first drill hole is created with the first drill on the bone surface. The first drill hole has a depth compatible with the length of the implant and a coronal area. A second drill is selected for creating a second hole having a width compatible with the body of the implant. A second drill hole is created on the bone surface with the second drill.

Another example is a set of drills to create an osteotomy on a bone surface for seating a dental implant having a body insertable in the osteotomy and a length. The set of drills includes a first drill having a tip to create a pilot hole, a first boring section to create a bore hole for a second drill and a second boring section to create a coronal area on the hole near the bone surface. The first drill has a length to create a hole compatible with the length of the implant and a coronal area. A second drill has a boring section for creating a second hole having a width compatible with the body of the implant.

Another example is a package for holding the components for a two drill protocol to create an osteotomy for an implant. The package includes a first drill having a tip to create a pilot hole, a first boring section to create a bore hole for a second drill and a second boring section to create a coronal area on the hole near the bone surface. The package includes a second drill for creating a second hole having a width compatible with the body of the implant. An implant having dimensions matching an osteotomy creatable by the first and second drills is provided. The package has a bottom container including a compartment storing the first drill, a compartment storing the second drill, and a compartment storing the implant. A top cover is mateable with the bottom container.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Figure 1A:
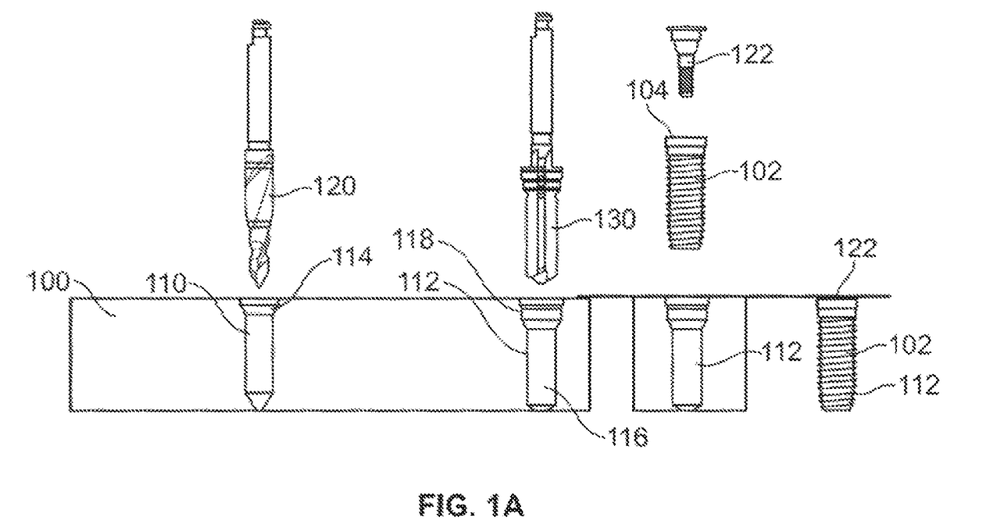
FIG. 1A is a cross-section view of a bone surface of a patient showing a two drill protocol to create an osteotomy for the seating of a straight walled implant having an internal countersink.

FIG. 1A is a cross-section view showing a two drill protocol to create an osteotomy in a bone surface 100 for seating a smooth wall implant 102 having a counter sink internal connection near a collar 104 at the top of the implant 102. FIG. 1A shows the process of creating a first stage hole 110 and a second stage hole 112 in the bone surface 100. As may be seen in FIG. 1A, after the second stage hole 112 is drilled in the bone surface 100, the implant 102 is seated in the created osteotomy. The first stage hole 110 is created by a first stage drill 120 which is used to mark the area for the osteotomy on the bone surface 100 to prevent the first stage drill 120 from walking. The first stage drill also creates the first stage hole 110 which has a depth corresponding to the length of the implant 102. The first stage hole 110 also has a coronal aspect 114 also created by the first stage drill 120 to accommodate a second stage drill 130. The second stage hole 112 is created by the second stage drill 130 which is used to widen the first hole 110 and create a bore 116 having a diameter that is compatible with the minor diameter of the implant 102.

The resulting osteotomy is created by the second stage hole 112 and has a depth that matches the length dimension of the appropriate dental implant 102. The dental implant 102 in this example is straight walled and has threads extending from a minor diameter of the body of the implant 102 creating a thread diameter. The diameter of the second stage hole 112 may be less than the diameter of the threads of the dental implant 102 so the threads may bite into the bone surface 100 to hold the dental implant 102 in the bone surface 100. In this example, the diameter of the bore 116 of the second stage hole 112 is substantially the same as the minor diameter of the implant 102. Alternatively, the bore 116 may have a diameter that is greater than the minor diameter of the implant 102 but less than the thread diameter of the implant 102. The second stage drill 130 is used to create a countersink internal connection area 118 in the second stage hole 112. In this example, a cover screw 122 is inserted in the countersink internal connection of the implant 102. As shown in FIG. 1A, the implant 102 and the inserted cover screw 122 are installed crestally at the same level of the bone surface 100. The countersink connection area 118 is also created to accommodate the collar 104 of the implant 102.

Figure 1B:
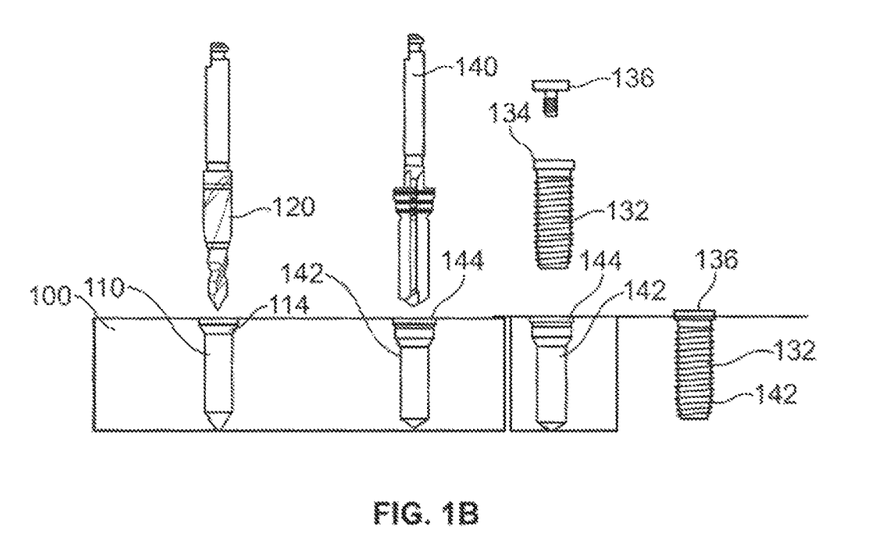
FIG. 1B is a cross-section view of a bone surface of a patient showing a two drill protocol to create an osteotomy for a straight walled implant having an external countersink.

FIG. 1B shows the steps of a two stage protocol for creating an osteotomy for a dental implant 132 similar to that of the protocol shown in FIG. 1A. FIG. 1B shows a second stage drill 140 which is a variation of the second stage drill 130 in FIG. 1A. The second stage drill 140 creates a second stage hole 142 having a countersink external connection area 144. The diameter of the second stage hole 142 matches the minor diameter of the body of the implant 132 The first stage of the protocol shown in FIG. 1B uses the same first stage hole 110 that is created by the first stage drill 120 in FIG. 1A. The second stage drill 140 has a diameter that matches the coronal aspect 114 created by the first stage drill 120.

The dental implant 132 has an external countersink in a collar 134 and is seated in the second stage hole 142 as shown in FIG. 1B. The dental implant 132 is straight walled and is mateable to a cover screw 136 which is inserted in the collar 134 of the dental implant 132. As shown in FIG. 1B, the cover screw 136 extends at a subscretal level above the surface of the bone surface 100 when the implant 132 is seated in the second stage hole 142 created by the two stage drill protocol. The countersink connection area 144 is also created to accommodate the collar 134 of the implant 132.

Figure 1C:
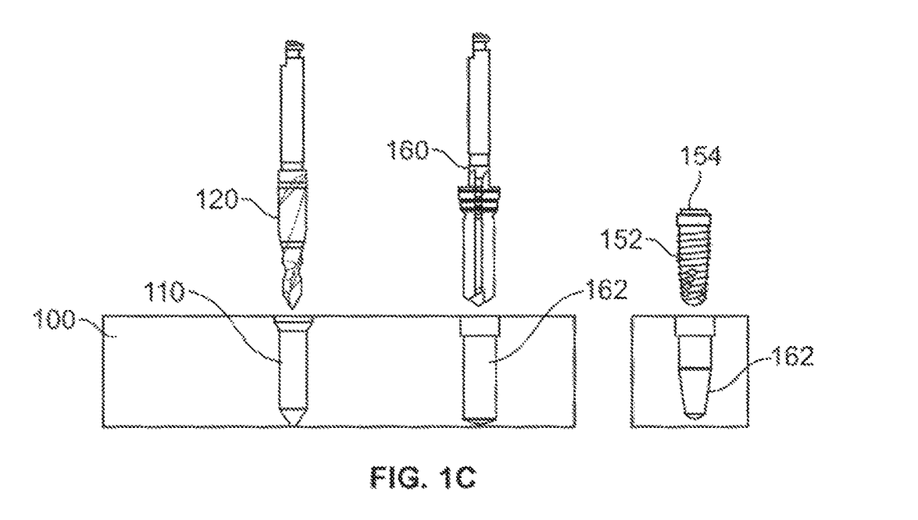
FIG. 1C is a cross-section view of a bone surface of a patient showing a two drill protocol to create an osteotomy for a tapered implant using a two drill protocol.

FIG. 1C shows a process of a two stage drill protocol to create an osteotomy for a tapered wall dental implant 152. FIG. 1C shows the bone surface 100 and a first stage hole 110 and a second stage hole 162 created by the drill protocol. In this example, the first stage hole 110 is identical to the first stage hole 110 in FIG. 1A and is created by the same first stage drill 120. After the first stage hole 110 is created by the first stage drill 120, a second stage drill 160 is used to create the second stage hole 162. The second stage hole 162 has a tapered base which matches the contours of the body of the tapered implant 152. The tapered implant 152 is seated in the second stage hole 162 in conjunction with a cover screw 154.

As will be explained below, the use of two drills in the protocols in FIGS. 1A-1C results in fewer steps to create the osteotomy to seat dental implants in the bone as each drill performs functions that were previously performed using multiple drills. Further, since fewer drills may be used, single use drills that are specific to a single implant of specific dimensions may be used efficiently thereby increasing cleanliness of the procedure.

Figure 2A:
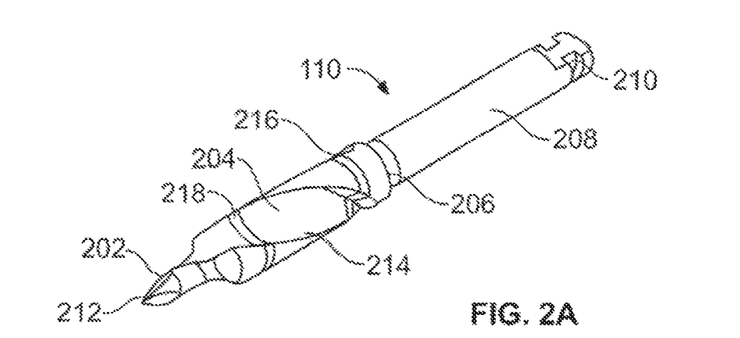
FIG. 2A is a perspective view of a first stage drill used in the two drill protocol shown in FIG. 1A.
Figure 2B:
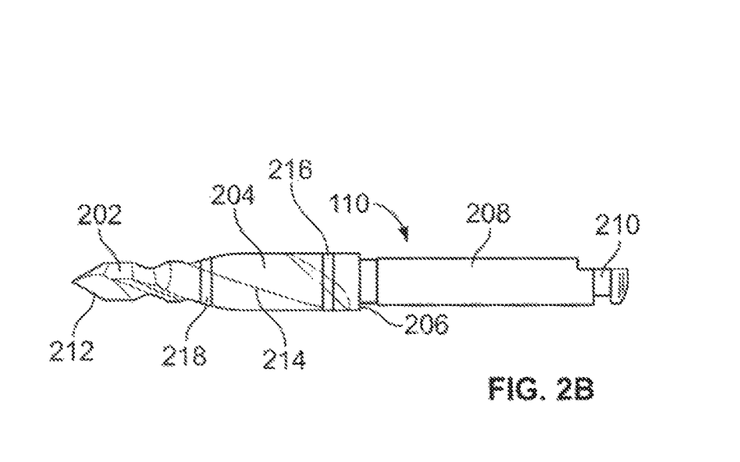
FIG. 2B is a side view of the first stage drill shown in FIG. 2A.

FIG. 2A is a perspective view and FIG. 2B is a side view of the first stage drill 120 used in the drill protocols of FIGS. 1A-1C. The first stage drill 120 has a series of features which allow the combination of functions performed previously by multiple drills. The first stage drill 120 includes a tip 202, a first stage boring section 204, a second boring section 206, a drive shaft 208 and an iso-latch section 210. The iso-latch section 210 is used to mate the drill 120 with a dental surgical motor unit or a dental surgical hand piece. The tip 202 includes angled blades 212 which are used to establish a pilot hole on the bone surface 100 in FIGS. 1A-1C. The angled blades 212 have an approximate 60 degree angle in this example, but the angled blades 212 may have other angles to facilitate cutting. The first stage boring section 204 in this example has a series of fluted cutting edges 214 which are used to cut into the bone to create the length of the first stage hole 110 in FIGS. 1A-1C. Other shapes and types of cutting edges, such as a four fluted perpendicular cutting edge arrangement, may be used. The second boring section 206 has a wider diameter than the first stage boring section 204 and creates the coronal aspect 114 in the first stage hole 110 which is used to guide the second stage drill 130 in FIG. 1A or the second stage drill 140 in FIG. 1B, or the second stage drill 160 in FIG. 1C. The second boring section 206 may include a circumferential laser mark 216 which indicates the approximate depth the drill 120 should be sunk in order to create a hole depth corresponding to the desired length of the matching implant such as the implant 102 in FIG. 1A. Additional laser marks such as a laser mark 218 may be provided as additional guides of how far to sink the drill 120 into the bone surface 100 to create the first stage hole 110 for implants of other lengths.

Figure 2C:
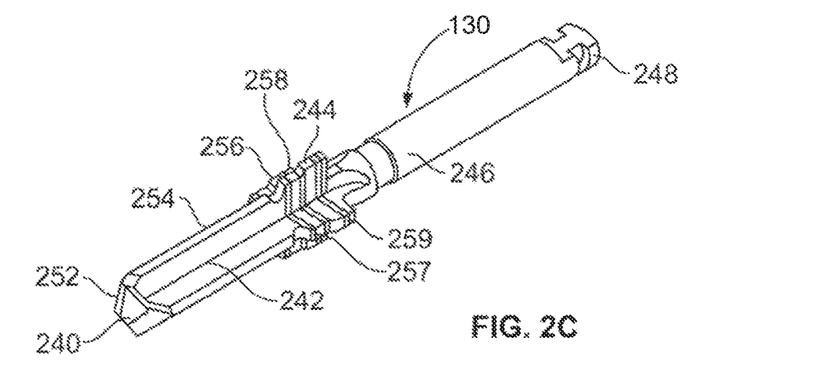
FIG. 2C is a perspective view of a second stage drill for creating an osteotomy for a straight walled implant having an internal countersink used in the protocol shown in FIG. 1A.
Figure 2D:
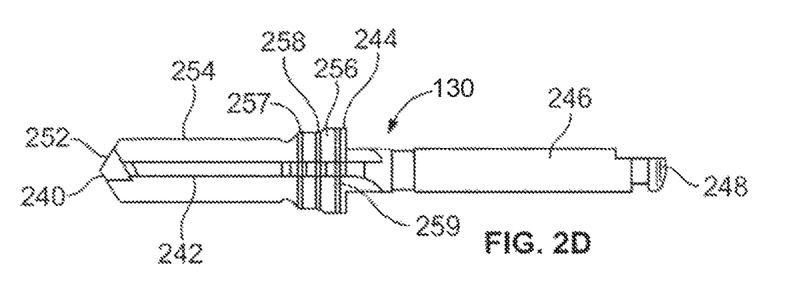
FIG. 2D is a side view of the second stage drill shown in FIG. 2C.

FIG. 2C is a perspective view and FIG. 2D is a side view of the second stage drill 130 in FIG. 1A which is used to create the second stage hole 112 for the straight walled implant 102. The second stage drill 130 includes a cutting tip 240, a first boring section 242, a countersink section 244, a drive shaft 246 and an iso-latch section 248. The iso-latch section 248 is used to attach the drill 130 to a dental surgical motor unit. The cutting tip 240 has angled cutting blades 252 which are arranged in a cross shape that assist in guiding the second stage drill 130 in the first stage hole 110. The first boring section 242 has four cutting blades 254 perpendicularly arranged which have an overall diameter compatible with the minor diameter of the implant 102 in FIG. 1A. The countersink section 244 is used to create the countersink area 118 of the second stage hole 112. The countersink section 244 has a series of tapered edges 256 that create the shape of the countersink area 118 in FIG. 1B. The countersink section 244 may include a laser mark 258 to assist in determining the depth to sink the drill 130 assuming the implant 102 is sunk at the crestal level of the bone surface 100.

The second stage drill 130 may have different features to perform the functions of creating a bore matching the diameter of the implant 102 and a counter sink area. For example, the cutting blades 254 may include notches. The cutting blades 254 may be replaced with blades in a twist shape. As shown in FIGS. 2C and 2D, the cutting blades 254 extend uniformly along the length of the first boring section 242. Alternatively, the cutting blades 254 may be tapered or profiled near the cutting tip 240. The countersink section 244 may have a blade that has a number of tapering stages or a single tapered edge. Alternatively, the countersink section may have a consistent diameter without any tapering. The countersink section 244 may have additional tapered blades and other laser marks to indicate subcrestal or supracrestal depths. For example, an additional laser mark 257 may be added to the countersink section 244 near the first boring section 242 to indicate a supracrestal depth. A laser mark 259 may be added to the countersink section 244 near the drive shaft 246 to indicate a subcrestal depth.

Figures 2E, 2F:
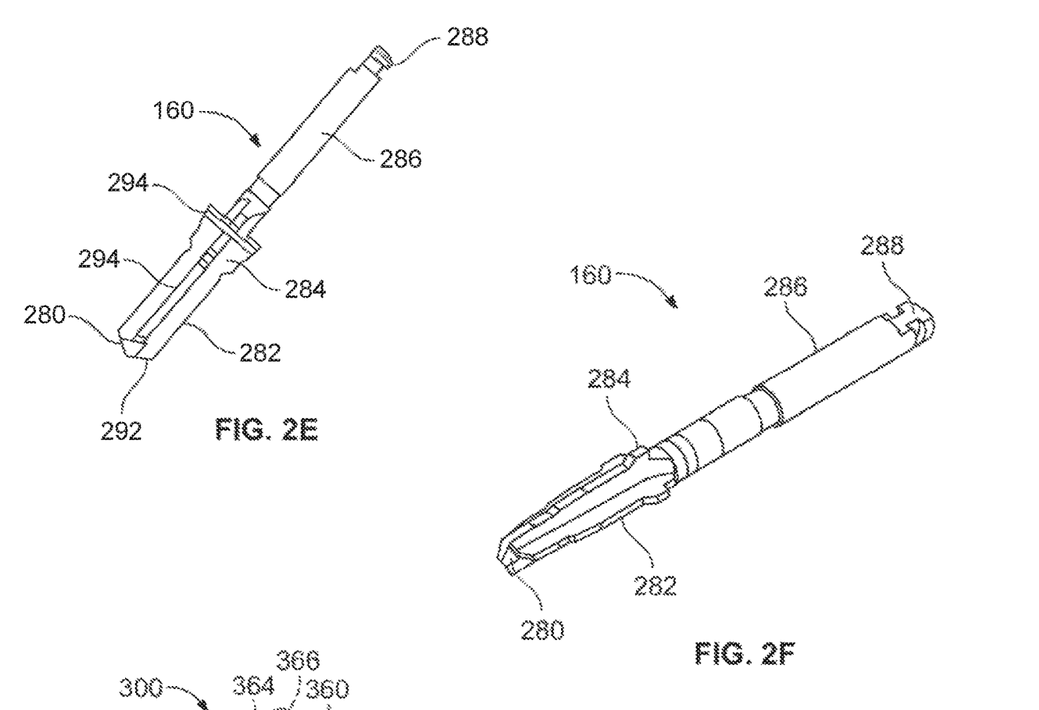
FIG. 2E is a side view of a second stage drill for creating an osteotomy for a tapered implant used in the protocol shown in FIG. 1C.
FIG. 2F is a perspective view of the second stage drill used in the two drill protocol shown in FIG. 1A.

FIG. 2E is a side view and FIG. 2F is a perspective view of the second stage drill 160 shown in FIG. 1C, The second stage drill 160 is used to create the second stage of the osteotomy shown in FIG. 1C that is fit for a tapered implant such as the implant 132. The second stage drill 160 includes a cutting tip 280, a boring section 282, a countersink section 284, a drive shaft 286 and an iso-latch section 288. The iso-latch section 288 is used to attach the drill 160 to a dental surgical motor unit. The cutting tip 280 has angled cutting blades 292 which are serrated in order to assist in creating the hole. The boring section 282 and the countersink section 284 have four cutting blades 294 in a perpendicular cross arrangement. The four cutting blades 294 of the boring section 282 have a bore diameter compatible with the minor diameter of the implant 152 in FIG. 1C. The cutting blades 294 of the first boring section 282 are tapered to match the shape of the implant 152 to create the tapered portion of the second stage hole 162.

Figure 3A:
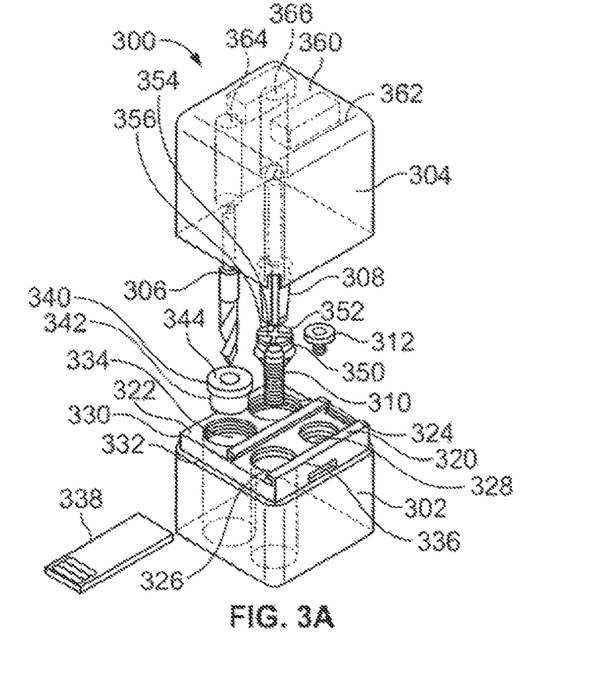
FIG. 3A is a perspective, exploded view of a package for drills used in a two stage protocol and a compatible implant.
Figure 3B:
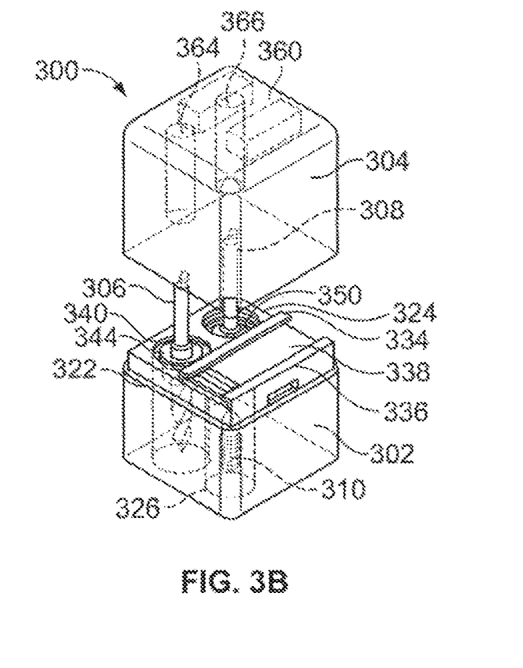
FIG. 3B is a perspective view of the package and drills in FIG. 3A, with the drills and the implant stored in the package.
Figure 3C:
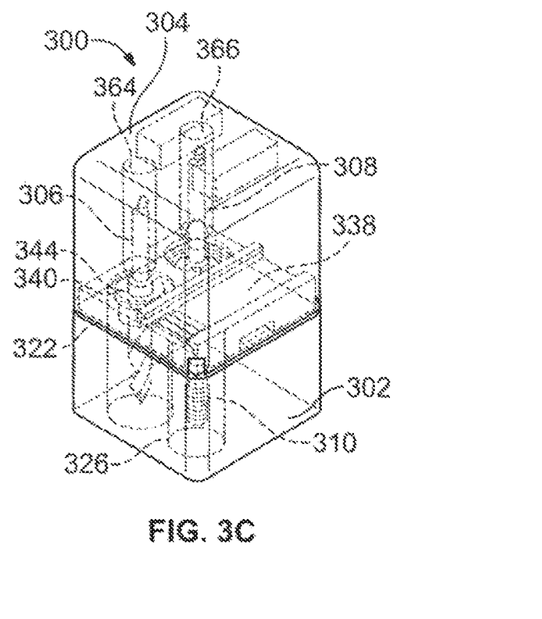
FIG. 3C is a perspective view of the package in FIG. 3A holding the drills and implant with the top cover and bottom container assembled.
Figure 3D:
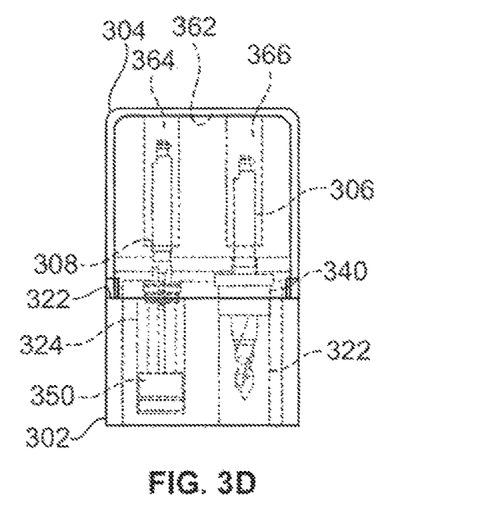
FIG. 3D is a side view of the assembled package in FIG. 3C.
Figure 3E:
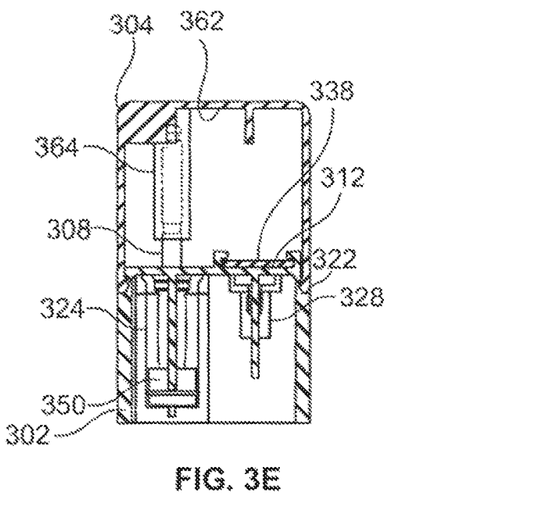
FIG. 3E is a side cross-section view of the assembled package in FIG. 3C.

The drills described above may be reused for another osteotomy having the same type of implant. However, the above described two stage drill protocol allows the use of packaging for the implant and the corresponding first and second stage drills. In this manner, the drills may be disposed of after a single use of creating an osteotomy for seating the implant. The joint package allows a clinician to have ready access to the appropriate drills for creating the osteotomy for a selected implant. FIG. 3A-3E show perspective views of the various components of a cubic shaped package 300 for holding the components for a two stage protocol for seating a dental implant in bone surface such as those described above in reference to FIGS. 1A-1C. The packaging system includes a bottom container 302 and a top cover 304 for holding components including a first stage drill 306, a second stage drill 308, an implant 310 and a cover screw 312 that may be used for the two drill protocol described above. FIG. 3A shows an exploded view of the components 306, 308, 310 and 312 removed from the package 300. FIG. 3B shows the package 300 with the components 306, 308, 310 and 312 stored and the cover 304 separated from the bottom container 302. FIG. 3C shows a perspective view of the top cover 304 fit on the bottom container 302 to enclose the components 306, 308, 310 and 312. FIG. 3D is a front view of the assembled package 300 in FIG. 3C and FIG. 3E is a cutaway view of the assembled package 300 in FIG. 3C. In this example, the drills 306 and 308 and implant 310 are used in a manner similar to the procedure described with reference FIG. 1B. However, it may be appreciated that the package 300 may be used with implants of any shape with matching drills such as those shown in FIG. 1A or 1C.

As may be seen in FIG. 3A-3E, the package 300 may be a rectangular shape but other shapes may be used. The bottom container 302 includes a top surface 320 that has four cylindrical compartments 322, 324, 326 and 328. The top surface 320 is attached to a raised area 330 which is recessed from the walls of the bottom container 302 to create a shelf surface 332. The shelf surface 332 is created on all four sides of the bottom container and supports the top cover 304 when it is attached to the bottom container 302. The top surface 320 includes two tracks 334 and 336 which hold a removable cover 338 to cover cylindrical compartments 326 and 328. In this example the cylindrical compartments 322 and 324 hold the first stage drill 306 and second stage drill 308 respectively. A cylindrical plug 340 has an outside surface 342 with a diameter to fit snuggly in the cylindrical compartment 322. The cylindrical plug 340 also has an interior through bore 344 that holds the second section of the first stage drill 306 as shown in FIG. 3B. Another cylindrical plug 350 has a top surface 352 with two perpendicular grooves 354 and 356 that mate with the cutting sections of the second stage drill 308. The cylindrical plug 350 slides into the bottom of the cylindrical compartment 324 and serves to secure the second stage drill 308 in the cylindrical compartment 324 as shown in FIG. 3B.

The implant 310 is inserted in the cylindrical compartment 326 in a sterile environment. The cover screw 312 is inserted in the cylindrical compartment 328. The cover 338 is held between the tracks 334 and 336 and slides on the tracks 334 and 326 to cover the cylindrical compartments 326 and 328 and thereby protect the implant 310 and the cover screw 312 from any contaminants when the top cover 304 is removed from the container bottom 302.

The top cover 304 includes a top panel 360 and four side walls. The top panel 360 includes an interior surface 362 from which two tubes 364 and 366 are suspending to match the cylindrical compartments 322 and 324 when the top cover 304 is attached to the bottom container 302. As shown in FIG. 3C-3E, when the top cover 304 is attached to the bottom container 302, the tube 364 encases the portion of the first stage drill 306 extending from the cylindrical compartment 322 and the tube 366 encases the portion of the second stage drill 308 extending from the cylindrical compartment 324.

The package 300 may include instructions or external markings on either the top cover 304 or the bottom container 302 that label a specifically dimensioned implant. The information may include the length and diameter of the enclosed implant. Since the package 300 includes the drills that are specifically matched to a particular implant, a clinician accessing the implant contained in the package 300 does not have to independently select appropriate drills for the seating of the implant.

The package 300 provides efficient storage of the implant 310 and appropriate drills 306 and 308 for a clinician. The package 300 protects the drills 306 and 308 via the top cover 304 until the clinician removes the top cover 304 and removes the drills 306 and 308 when they are needed for the two stage drill protocol. In addition, after the top cover 304 is removed, the cover 338 insures that the implant 310 and cover screw 312 remain protected from contaminants until the osteotomy is completed with the two drills 306 and 308. In the two stage protocol such as that shown in FIG. 1B, a clinician opens the package 300 by removing the top cover 304. The clinician then removes the first drill 306 from the cylindrical compartment 322 and install the first drill 306 on a dental surgical motor unit to create the first stage hole such as the first stage hole 110 in FIG. 1B. The clinician then discards the first drill 306. The clinician removes the second stage drill 308 from the cylindrical compartment 324 and installs the second stage drill 308 on the dental surgical motor unit to create the second stage hole 142 in FIG. 1B. The clinician may then discard the second stage drill 308. Since the osteotomy has now been created, the clinician slides the cover 338 back on the tracks 334 and 336 to access the cylindrical compartments 326 and 328. The clinician may then remove the implant 310 for seating in the osteotomy with minimal exposure to contaminants. The clinician may use a tool such as an open end wrench in conjunction with an implant mount to pick up the implant 310 and remove it from the cylindrical compartment 326. The clinician then seats the implant 310 in the osteotomy and uses a driving tool such as a ratchet to screw in the implant 310. After the implant 310 is seated, the clinician removes the cover screw 312 from the cylindrical compartment 328 with an implant driver and places the cover screw 312 into the seated implant 310.

Figure 4A:
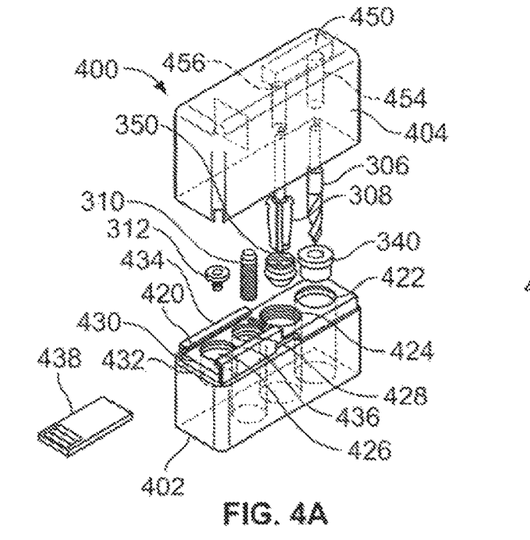
FIG. 4A is a perspective, exploded view of an alternate package for drills used in a two stage protocol and a compatible implant.
Figure 4B:
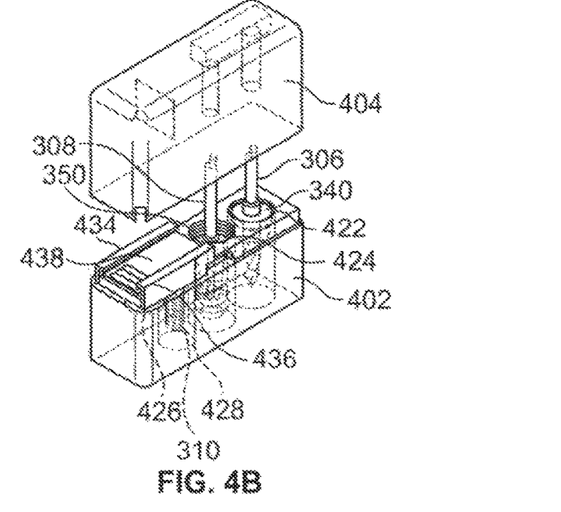
FIG. 4B is a perspective view of the package and drills in FIG. 4A, with the drills and implant stored in the package.
Figure 4C:
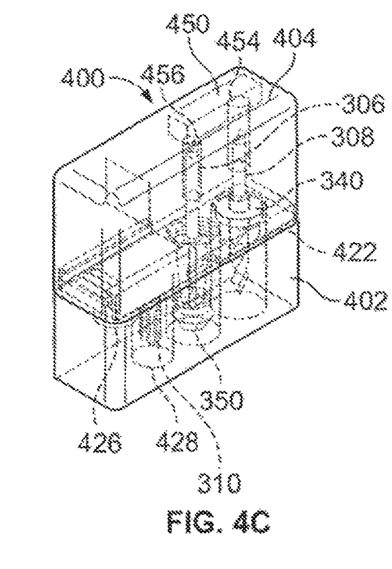
FIG. 4C is a perspective view of the package in FIG. 4A holding the drills and implant with the top cover and bottom container assembled.
Figure 4D:
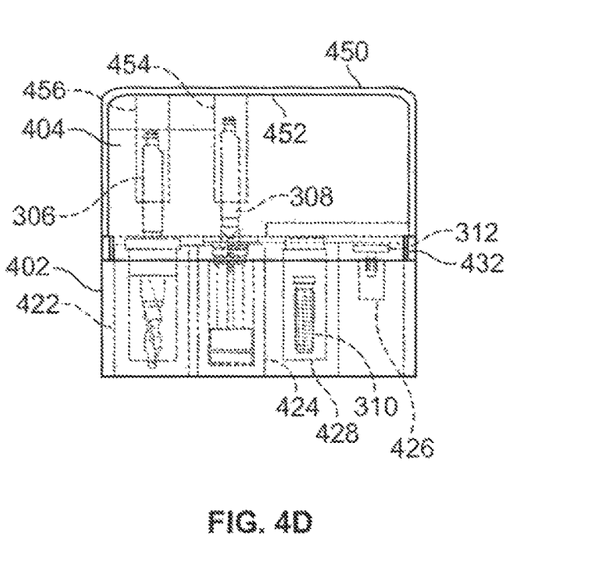
FIG. 4D is a side view of the assembled package in FIG. 4C.
Figure 4E:
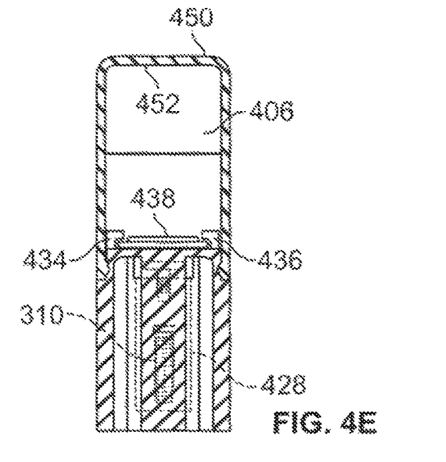
FIG. 4E is a side cross-section view of the assembled package in FIG. 4C.

An alternate package for the components for the two stage protocol may be an in-line type package 400 shown in FIGS. 4A-4E. FIGS. 4A-4E show perspective views of the various components of an alternative arrangement for storing the components (drills 306 and 308, implant 310 and cover screw 312 in FIG. 3A) for a two stage protocol for seating a dental implant in bone surface such as those described above in reference to FIGS. 1A-1C. The in-line package 400 includes a bottom container 402 and a top cover 404 for holding the components of the first stage drill 306, the second stage drill 308, the implant 310 and the cover screw 312. FIG. 4A shows an exploded view of the components 306, 308, 310 and 312 contained in the package 400, FIG. 4B shows the package 400 with the components 306, 308, 310 and 312 stored with the top cover 404 off and FIG. 4C shows a perspective view of the top cover 404 when attached to the bottom container 402. FIG. 4D is a front view of the assembled package 400 in FIG. 4C and FIG. 4E is a cutaway view of the assembled package 400 in FIG. 4C.

The bottom container 402 includes a top surface 420 that has four cylindrical compartments 422, 424, 426 and 428. The top surface 420 is attached to a raised area 430 which is recessed from the walls of the bottom container 402 to create a shelf surface 432 that contacts the walls of the top cover 404 when the top cover 404 is attached to the bottom container 402. The top surface 420 includes two tracks 434 and 436 which hold a removable cover 438 to cover cylindrical compartments 426 and 428. In this example the cylindrical compartments 422 and 424 hold the first stage drill 306 and second stage drill 308 respectively. As with the package 300 in FIGS. 3A-3E, the first stage drill 306 is inserted in a cylindrical plug 340 which is inserted in the cylindrical compartment 422. The other cylindrical plug 350 has grooves that mate with the cutting sections of the second stage drill 308. The cylindrical plug 350 slides into the cylindrical compartment 424 and serves to hold the second stage drill 308 upright in the cylindrical compartment 424 as shown in FIG. 4B.

The implant 310 is inserted in the cylindrical compartment 428 in a sterile environment. The cover screw 412 is inserted in the cylindrical compartment 426. The cover 438 is held between the tracks 434 and 436 to cover the compartments 426 and 428 and thereby protect the implant 310 and the cover screw 312 from any contaminants when the top cover 404 is removed from the container bottom 402.

The top cover 404 includes a top plate 450 and four side walls. The top plate 450 includes an interior surface 452 which mounts two tubes 454 and 456 which are located in proximity with the cylindrical compartments 422 and 424. As shown in FIG. 4C-4E, when the top cover 404 is mated with the bottom container, the tube 454 encases the portion of the first stage drill 306 that extends from the surface 420 and the tube 456 encases the portion of the second stage drill 308 that extends from the surface 420.

Figure 5:
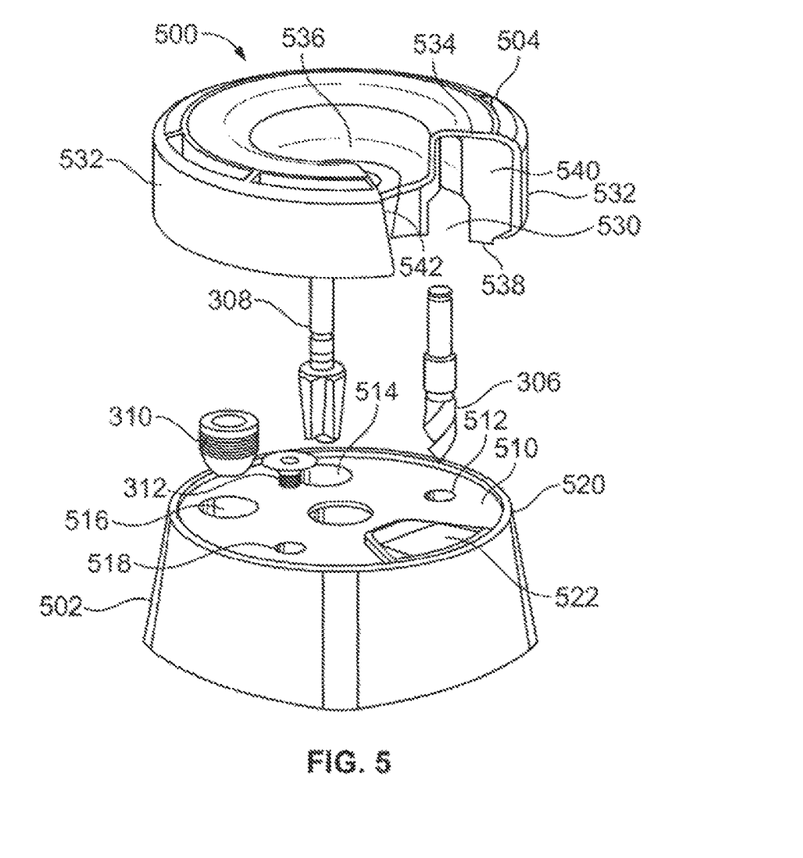
FIG. 5 is a perspective view of another alternate package for drills used in a two stage protocol and a compatible implant.

Another alternate package for the components for the two stage protocol may be a cylindrical rotational type package 500 shown in FIG. 5. FIG. 5 shows the package 500 storing the components (drills 306 and 308, implant 310 and cover screw 312 in FIG. 3A) for a two stage protocol for seating a dental implant in bone surface such as those described above in reference to FIGS. 1A-1C. The cylindrical package 500 includes a bottom cylindrical container 502 and a rotatable top cover 504 for holding the components of the first stage drill 306, the second stage drill 308, the implant 310 and the cover screw 312.

The bottom container 502 is generally cylindrical in shape and includes a circular top surface 510 that includes four cylindrical compartments 512, 514, 516 and 518 extending through the body of the bottom container 502. The top surface 510 is bounded by a circumferential ridge 520 which extends around the perimeter of the bottom container 502. The top surface 510 also has a label area 522 which may be used for information on the stored implant 310 such as dimensions or other informational text or graphics.

The top cover 504 is generally toroidally shaped with the same diameter of the bottom container 502. The top cover 504 includes a gap 530 which is roughly trapezoid shaped. The top cover 504 includes a curved outer sidewall 532 which extends around most of the perimeter of the top cover 504 except for the gap 530. A circular top surface 534 includes a center circular depression 536. The top cover 504 also includes a semi-circular bottom surface 538 which mates with the circumferential ridge 520 which allows the top cover 504 to be rotated relative to the bottom container 502. The outer sidewall 532 terminates in two lateral facing surfaces 540 and 542 which form the gap 530.

The gap 530 of the top cover 504 allows a user access to the cylindrical compartments 512, 514, 516 and 518 on the top surface 510 of the bottom container. As the top cover 504 is rotated relative to the bottom container 502, each cylindrical compartment 512, 514, 516 and 518 may be accessed when the gap 530 is rotated over it. Thus, the clinician needs to only rotate the top cover 504 to remove the required component during each stage of the osteotomy process and the seating of the implant 310. During these procedures, the top cover 504 covers the other compartments thereby protecting the stored components against contaminants.

When the package 500 is stored, the gap is located over the label area 522. When the clinician begins the two stage process, the clinician rotates the top cover 504 so the gap 530 aligned to allow access to the first cylindrical container 512. The first drill 306 may be removed and used for the drilling the first stage hole. The clinician may then rotate the top cover 504 so the gap 530 is aligned to allow access to the second cylindrical container 514. The second stage drill 308 may then be removed and used to create the second stage hole. The clinician may then rotate the top cover 504 so the gap 530 is aligned to allow access to the cylindrical container 516 holding the implant 310. The clinician may then remove the implant 310 and seat it in the created osteotomy. Finally, the clinician may rotate the top cover 504 so the gap 530 is aligned to allow access to the last cylindrical container 518 holding the cover screw 312. The cover screw 312 may then be removed an inserted into the seated implant 310.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A method of creating tapered osteotomy on a bone surface for seating a tapered dental implant having a body insertable in the tapered osteotomy and a length, the method comprising:

selecting a first drill having a front end and an opposite latch end, the first stage drill including a tip section at the front end with blades shaped to create a pilot hole penetrating the bone surface without the first drill walking, a first boring section located between the tip section and the opposite latch end, the first boring section having a predetermined diameter to create a bore hole for a second stage drill and a second boring section located between the latch end and the first boring section, the second boring section having cutting edges to create a coronal area near the bone surface, the cutting edges including a visual mark to indicate the depth the first drill should be sunk, the first stage drill having a length between the first and second boring sections compatible with at least the length of the tapered dental implant and having a substantially circular coronal area;

creating a first drill hole on the bone surface having a depth compatible with the length of the tapered dental implant and a coronal area with the first drill;

selecting a second drill for creating a second hole having a width compatible with the body of the tapered dental implant, the second drill including a tip, a first boring section adjacent to the tip, and a second boring section adjacent to the first boring section, the first boring section for creating a second hole having the tapered osteotomy with a width compatible with the body of the tapered dental implant and the second boring section for creating a second coronal area near the bone surface, the first and second boring sections having a plurality of cutting edges, each of the cutting edges perpendicular to at least one of the other plurality of cutting edges, wherein a first diameter along the first boring section includes a tapered section tapering from a first maximum diameter, away from the second boring section, to a first minimum diameter, wherein a second minimum diameter of the second boring section is greater than the first maximum diameter of the tapered section, and wherein the second boring section includes a number of tapering stages; and creating a second drill hole on the bone surface with the second drill.

2. The method of claim 1, wherein the first and second drills are disposable after a single use.

3. The method of claim 1, wherein the first and second drills are reusable for creating another osteotomy.

4. The method of claim 1, further comprising inserting the tapered dental implant in the tapered osteotomy created by the first and second drills.

5. The method of claim 1, wherein the first boring section of the first drill includes either twisted cutting edges or perpendicular cutting edges.

6. The method of claim 1, wherein the second drill includes tapered sides to match a tapered dental implant.

7. The method of claim 1, wherein the coronal area is created for an internal countersink for a cover screw mated with the tapered dental implant.

8. The method of claim 1, wherein the coronal area is created for an external countersink for a cover screw mated with the tapered dental implant.

9. A drilling system, comprising:
a package for holding:
a first stage drill having a front end and an opposite latch end, the first stage drill including a tip section at the front end with blades shaped to create a pilot hole penetrating the bone surface without the first drill walking, a first boring section located between the tip section and the opposite latch end, the first boring section having a predetermined diameter to create a bore hole for a second stage drill and a second boring section located between the latch end and the first boring section, the second boring section having cutting edges to create a coronal area near the bone surface, the cutting edges including a visual mark to indicate the depth the first drill should be sunk, the first stage drill having a length between the first and second boring sections compatible with at least the length of the tapered dental implant and having a substantially circular coronal area; and
a second stage drill having a tip, a first boring section adjacent to the tip, and a second boring section adjacent to the first boring section, the first boring section for creating a second hole having the tapered osteotomy with a width compatible with the body of the tapered dental implant and the second boring section for creating a second coronal area near the bone surface, the first and second boring sections having a plurality of cutting edges, each of the cutting edges perpendicular to at least one of the other plurality of cutting edges, wherein a first diameter along the first boring section includes a tapered section tapering from a first maximum diameter, away from the second boring section, to a first minimum diameter, wherein a second minimum diameter of the second boring section is greater than the first maximum diameter of the tapered section, and wherein the second boring section includes a number of tapering stages; and
a tapered dental implant having dimensions matching a tapered osteotomy creatable by the first and second drills,
wherein the package comprises:
a bottom container including a compartment storing the first drill, a compartment storing the second drill, and a compartment storing the tapered dental implant; and
a top cover mateable with the bottom container.

10. The drilling system of claim 9, wherein the compartments for the first and second drills are cylindrically shaped.

11. The drilling system of claim 9, further comprising a cover screw compatible with the tapered dental implant, wherein the bottom container includes a compartment for the cover screw.

12. The drilling system of claim 9, further comprising a cover sealing the compartments for the tapered dental implant when the top cover is removed from the bottom container.

13. The drilling system of claim 9, further comprising a plug having an internal bore to hold the first drill and side surfaces to suspend the plug when inserted in the compartment for the first drill.

14. The drilling system of claim 9, further comprising a plug having groves to mate with the cutting edges of the second drill, the plug insertable in the compartment for the second drill.

15. The drilling system of claim 9, wherein the top cover includes a bottom surface including two tubes extending therefrom to cover the first and second drills when the top cover is mated to the bottom container.

16. The drilling system of claim 9, wherein the bottom container is cylindrically shaped and the top cover is cylindrically shaped and includes a gap, wherein the top cover is rotatable relative to the bottom container when the top cover is mated with the bottom compartment and wherein the gap allows access to each of the compartments as the top cover is rotated.

17. A drilling system to create a tapered osteotomy on a bone surface using only two drills, the tapered osteotomy for seating a tapered dental implant, the tapered dental implant having a body insertable in the tapered osteotomy and a length, the drilling system comprising:
a first stage drill having a front end and an opposite latch end, the first stage drill including a tip section at the front end with blades shaped to create a pilot hole penetrating the bone surface without the first drill walking, a first boring section located between the tip section and the opposite latch end, the first boring section having a predetermined diameter to create a bore hole for a second stage drill and a second boring section located between the latch end and the first boring section, the second boring section having cutting edges to create a coronal area near the bone surface, the cutting edges including a visual mark to indicate the depth the first drill should be sunk, the first stage drill having a length between the first and second boring sections compatible with at least the length of the tapered dental implant and having a substantially circular coronal area; and
a second stage drill having a tip, a first boring section adjacent to the tip, and a second boring section adjacent to the first boring section, the first boring section for creating a second hole having the tapered osteotomy with a width compatible with the body of the tapered dental implant and the second boring section for creating a second coronal area near the bone surface, the first and second boring sections having a plurality of cutting edges, each of the cutting edges perpendicular to at least one of the other plurality of cutting edges, wherein a first diameter along the first boring section includes a tapered section tapering from a first maximum diameter, away from the second boring section, to a first minimum diameter, wherein a second minimum diameter of the second boring section is greater than the first maximum diameter of the tapered section, and wherein the second boring section includes a number of tapering stages.

18. The drill system of claim 17, wherein the first and second stage drills are disposable after a single use.

19. The drilling system of claim 17, wherein the first and second stage drills are reusable for creating another osteotomy.

20. The drilling system of claim 17, wherein the first boring section of the first stage drill includes twisted cutting edges or perpendicular cutting edges.

21. The drilling system of claim 20, wherein the first and second stage drills each include four cutting edges.

22. The drilling system of claim 17, wherein the drilling system further includes a tapered dental implant and packaging including a package for holding the first and second drill and the tapered dental implant, the package having a bottom container including a compartment storing the first drill, a compartment storing the second drill, and a compartment storing the tapered dental implant, and a top cover mateable with the bottom container.

23. The drilling system of claim 17, wherein the drilling system further includes a tapered dental implant and packaging including a cover screw compatible with the tapered dental implant.

24. The drilling system of claim 17, wherein the boring section of the second stage drill includes a mark to indicate the depth the second stage drill should be sunk.

25. The drilling system of claim 17, wherein the second boring section of the second stage drill includes a number of tapering stages.

26. The drilling system of claim 17, wherein the second boring section of the second stage drill includes a single taper.

* * * * *